（12) United States Patent
Drevillon et al.

(10) Patent No.: US 6,175,412 B1
(45) Date of Patent: Jan. 16, 2001

(54) OPTICAL COMPONENT FOR POLARIZATION MODULATION, A MUELLER POLARIMETER AND ELLIPSOMETER CONTAINING SUCH AN OPTICAL COMPONENT, A PROCESS FOR THE CALIBRATION OF THIS ELLIPSOMETER, AND AN ELLIPSOMETRIC MEASUREMENT PROCESS

(75) Inventors: Bernard Drevillon, Clamart; Eric Compain, Huismes, both of (FR)

(73) Assignee: Centre National de la Recherche Scientifique, Paris (FR)

( * ) Notice: Under 35 U.S.C. 154(b), the term of this patent shall be extended for 0 days.

(21) Appl. No.: 09/091,400

(22) PCT Filed: Oct. 16, 1997

(86) PCT No.: PCT/FR97/01849

§ 371 Date: Oct. 6, 1998

§ 102(e) Date: Oct. 6, 1998

(87) PCT Pub. No.: WO98/19142

PCT Pub. Date: May 7, 1998

(30) Foreign Application Priority Data

Oct. 25, 1996 (FR) .................................................. 96 13081

(51) Int. Cl.[7] ...................................................... G01J 4/00

(52) U.S. Cl. .......................................... 356/369; 359/278

(58) Field of Search ..................................... 356/364, 365, 356/366, 367, 368, 369; 250/225; 359/561, 256, 277, 278

(56) References Cited

U.S. PATENT DOCUMENTS 4,306,809 12/1981 Azzam .
5,956,147 * 9/1999 Jellison , Jr. et al. ................ 356/369

OTHER PUBLICATIONS

J.O. Stenflo et al: "Demodulation of All Four Stokes Parameters With a Single CCD: ZIMPOL II—Conceptual Design", Lest Technical Report No. 54, Institute of Theoretical Astrophysics, University of Olso, 1992, p. 13, line 5 to line 10.
H. Povel: "Imaging Stokes Polarimetry with Piezoelastic Modulators and Charge–Coupled Device Image Sensors", Optical Engineering, vol. 34, No. 7, Jul., 1995, Bellingham U.S., pp. 1870–1878.
P.S. Hauge: "Recent Developments in Instrumentation in Ellipsometry", Surface Science, vol. 96, 1980, pp. 108–140.
R.M.A. Azzam et al: "Construction, Calibration and Testing of a Four–Detector Photopolarimeter", Review of Scientific Instruments, vol. 59, No. 1, Jan., 1988, New York, U.S, pp. 84–88.
R.C. Thompson et al: "Measurement of Polarized Light Interactions Via the Mueller Matrix", Applied Optics, vol. 19, No. 8, Apr. 15, 1980, New York, U.S, pp. 1323–1332.

* cited by examiner

Primary Examiner—Hoa Q. Pham
(74) Attorney, Agent, or Firm—Arent Fox Kintner Plotkin & Kahn, PLLC

(57) ABSTRACT

An optical component for modulation of polarization, a Mueller polarimeter and ellipsometer containing such an optical component. The optical component modulates a linearly polarized incident beam and returns a modulated beam. It includes a coupled phase modulator which modulates the incident beam twice in succession, the two modulations having the same frequency of $\omega/2\pi$, and a coupling system modifying the polarization state of the light between the two modulations. The ellipsometer includes the means for detection of a measurement beam returned by a sample, which receives the modulated beam, in addition to a processing unit. The means of detection include a polarimeter producing n measured quantities representing the polarization states of the beam, and the processing unit produces m values for each of these quantities by Fourier transform, with $n \times m \geq 16$ and $m \geq 4$, providing simultaneous access to the sixteen components of the Mueller matrix of the sample.

19 Claims, 4 Drawing Sheets

US 6,175,412 B1

OPTICAL COMPONENT FOR POLARIZATION MODULATION, A MUELLER POLARIMETER AND ELLIPSOMETER CONTAINING SUCH AN OPTICAL COMPONENT, A PROCESS FOR THE CALIBRATION OF THIS ELLIPSOMETER, AND AN ELLIPSOMETRIC MEASUREMENT PROCESS

BACKGROUND OF THE INVENTION

The subject of this invention is an optical modulation component, a Meuller polarimeter and ellipsometer containing such an optical component, a process for the calibration of this ellipsometer, and an ellipsometric measurement process.

In order to measure the magnitudes which are representative of a sample, such as optical, physical, chemical or electrical magnitudes, it is conventional to make use of an ellipsometer. However the field of application of the standard ellipsometer is restricted to non-depolarising, isotropic materials, presenting a plane interface. The ordinary ellipsometer is used to measure non-isotropic materials, but only if they are non-depolarising. Now the current requirements of industrial companies, biologists and chemists frequently concern polarising materials, such as those with rough or speckled surfaces.

A Mueller ellipsometer (or Mueller Matrix Ellipsometer—MME) makes it possible to measure in any medium. In fact the polarisation states of the light can be represented by a 4th dimension vector, which is conventionally the Stokes light vector (S). A description of this can be found in the work of Azzam and Bashara entitled "ellipsometry and polarised light", North-Holland, pp. 55–60. The Stokes vector consists of the I, Q, U and V coordinates, respectively representing the mean intensities of the four different polarisation states. Any medium can then be represented by a real matrix in 4×4 dimensions which describes the couplings in intensity of the different polarisation modes of the light, these couplings being provoked by the interaction of the light with the medium. This matrix, known as the Mueller M, includes sixteen coefficients which are generally independent of each other. The Mueller ellipsometer is able to measure the full Mueller matrix of the medium under study. It is therefore particularly applicable to deposits on rough surfaces or measurement on particles, for which other ellipsometric measurement processes are not appropriate.

The arrangements employed for Mueller ellipsometry or Mueller ellipsometers commonly include a light source, a polarisation states generator (or PSG) and a polarisation states detector (PSD) which is also called a polarimeter. A detailed description of these can be found in the article by P. S. Hauge entitled "Recent developments in instrumentation in ellipsometry", Surface Science, vol. 96, pp. 108–140, 1980. In operation, a light beam is emitted from the source, the beam is given polarisation states using the PSG, the beam is sent to the sample to be measured, and the resulting beam is detected using the PSD. Polarisers and quarter-wave blades fixed in the PSG and the PSD are also known to be used, assigning sixteen different configurations to them, in order to measure the Mueller matrix of the sample. This manual technique is difficult to use however, and not very effective.

In "Photopolarimetric measurement of the Mueller matrix by Fourier analysis of a single detected signal", R. M. Azzam, Optics Letters, vol. 2, No.6, pp. 148–150, 1978, a Mueller ellipsometer was proposed in which the PSG and the PSD respectively included two quarter-wave blades revolving at $\omega$ and $5\omega$. The sixteen coefficients of the Mueller matrix (W)ere then extracted from the first sixteen harmonics of the frequency $\omega$ of the detected signal. This arrangement had the disadvantage of being restricted to very low frequencies, and to require the use of a "chopper" in order to eliminate the ambient background noise.

In "Mueller-matrix (M)easurement using the four-detector photopolarimeter", R. M. Azzam, Optics Letters, vol. 11, No. 5, pp. 270–272, 1986, Mueller ellipsometers were proposed with a multi-channel PSD and a rotating delay device in the PSG. These devices were also limited to low modulation frequencies, typically necessitating several seconds for acquisition.

In "Measurement of Mueller matrices", R. Anderson, Applied Optics, vol. 31, p. 11, 1992, a single-channel ellipsometer was also proposed which included a high-frequency polarisation modulator in the PSG and the PSD. However several configurations had to be combined in order to get a complete measurement.

In "Measurement of polarised light interactions via the Mueller matrix", Randall C. Thompson et al., Applied Optics, vol. 19, No. 8, pp. 1323–1332, 1980, a high-frequency ellipsometer was envisaged using four electoro-optical phase modulators at different frequencies and sixteen synchro-detectors. This arrangement had the disadvantages of being expensive and complicated to implement, in addition to being sensitive to noise since the continuous component of the signal was not modulated.

An article in LEST Technical Report by Stenflo et al., No. 54, XP000645515, 1992, and another in the Optical Engineering Review by Povel, vol. 34, No. 7, XP000517055, pp. 1870–1878, revealed a system for simultaneous measurement of the four Stokes parameters, and its application to polarimetry. The measurement system includes two piezzo-elastic modulators operating at the same frequency, coupled in phase and with an angular shift of 45° in their orientations, a super-achromatic $\lambda/4$ plate, and a linear polariser, with the modulators, the plate and the polariser placed successively on an optical track.

This system gave rise to problems with synchronisation of the modulators and with control over their coupling. It also had the drawback of being sensitive to noise.

OBJECTS AND SUMMARY OF THE INVENTION

This present invention concerns a Mueller ellipsometer which can be used at high frequency, which is easy to implement, and which gives simultaneous and accurate measurements of the sixteen coefficients of the Mueller matrix.

The invention also concerns such an ellipsometer which, separately or cumulatively, can be insensitive to ambient noise, provide its spectroscopic capacities, allow modulation at frequencies as high as 100 MHz, and be usable for measurements in real time such as the growth of layers on a substrate.

In addition, the invention has as an objective a process for the calibration of a Mueller ellipsometer as covered by the invention, this process being at once precise, rapid and easy to implement.

Another purpose of the invention is a Mueller ellipsometric measurement process which is easy to implement, which provides simultaneous and precise measurement of the sixteen coefficients of the Mueller matrix, and which can be used at high modulation frequencies.

The invention also covers an optical modulation component which can be used in the PSG, and also in the PSD where appropriate, of a Mueller ellipsometer. More generally, the invention concerns an optical modulation component which can be used for high frequency modulation and which is simple to implement.

The invention also covers a PSD or polarimeter which can be used in any device requiring measurement of the polarisation of light, and particularly in the Mueller ellipsometer, capable of being employed at high frequencies and easy to use.

To this end, the invention includes an optical component for polarisation modulation including a polarisation modulator which modulates an incident wave of linearly polarised light, and returns a modulated beam. The polarisation modulator is a coupled phase modulator modulating the incident wave twice in succession, the two modulations being strictly at the same frequency of $\omega/2\pi$, and being coupled.

According to the invention, the modulations are coupled by a system which modifies the state of polarisation of the light between the two modulations.

The two modulations are "strictly" at the same frequency in the sense that they have a relative phase difference between them which is fixed in time, and which therefore undergoes no movement in relation one to the other. This strict identity of frequency is preferably obtained by an external slaving arrangement or by a double use of the same modulator.

By "coupled modulations" is meant identical modulations (that is with the same frequency and a relative phase difference fixed in time) which are not reducible to a single phase modulation. Thus the two modulations do not apply to the same components of the Stokes vector. More accurately, since each phase modulation is applied in accordance with a two-dimensional vectorial sub-space of the four-dimensional polarisation vectorial space in which the Stokes vector of the incident beam is defined, the two sub-spaces associated respectively with the two modulations are not confused.

The modulations are coupled by means of a coupling system, and not by a simple angular difference between the directions of modulation.

It is preferable that the coupling system should be of the partial polariser and phase shifter (PPS) type.

The phase modulator is said to be "coupled" by reference to the two coupled phase modulations which it applies.

In mathematical terms, the optical component applies a polarisation modulation such that the Stokes vector (S) of the modulated beam is expressed linearly as a function of a harmonic base of the $\omega$ pulse by a rank 4 matrix.

According to a preferred method of realisation of the optical component according to the invention, the coupled modulator includes a phase modulator producing two successive modulations and a coupling system of the partial polariser and phase shifter type. The phase modulator produces the first modulation, and sends the incident wave to the same coupling system. The coupling system sends the incident wave to the phase modulator, and the phase modulator produces the second modulation.

This method of realisation is particularly advantageous in that it produces modulation at high frequency of the four components of the Stokes vector, including the mean intensity (1). As a result, when it is used in a PSG, it provides a low detection level and renders the use of a chopper unnecessary.

Furthermore, it requires only a single phase modulator to perform the two modulations. It therefore avoids problems of synchronisation involving an absolute phase control. In particular, it allows the use of a photo-elastic modulator, which supplies an extended range of wavelengths (from 0.2 $\mu$m to 19 $\mu$m), a large optical window (greater than 1 cm) and a low dependence on temperature variations.

With this method of realisation, it is preferable that the phase modulator and the coupling system be respectively oriented at 45° and 90° from the direction of polarisation, since the light of the incident beam is polarised linearly according to one polarisation direction.

In another preferred method of realisation of the optical component according to the invention, the coupled modulator includes two phase modulators respectively producing the same two successive modulations, with the two phase modulators having the same orientation, and a coupling system including a partial polariser and a phase shifter a interposed between the two phase modulations. The coupling system sends the incident beam from the first to the second of the phase modulators.

The two phase modulator should preferably be of the opto-electrical type.

This other method of realisation can be used to modulate the four components of the Stokes vector at high frequency, as with the first method of realisation.

By stating that the coupling system "sends" the incident wave, one means that it can either transmit it or reflect it.

It is preferable in this other method of realisation that the phase modulators on the one hand, and the coupling system on the other, should be oriented respectively at 45° and 90° to the direction of polarisation, since the light of the incident wave is polarised linearly according to one direction of polarisation.

It is advantageous if the coupling system operates on reflection, and includes a first partial polarisation element and a second phase-shift and reflection element. According to a preferred form of this coupling system, the first element is made up by stacking air-glass interfaces at the Brewster angle, and the second element is composed of a prism.

The invention also covers a polarimeter which includes an optical component according to the invention.

Such a PSD or polarimeter can be employed, for example, in a Mueller ellipsometer, where the PSG includes a polarisation modulator.

The invention also concerns a Mueller ellipsometer intended for the measurement of a sample, represented by the coefficients of a Mueller matrix. The ellipsometer includes:

- a light source emitting an incident light beam,
- a polariser, linearly polarising the incident beam,
- a polarisation modulator modulating the incident beam, and the modulated incident beam returning the measurement beam,
- means to detect the measurement beam, producing electrical signals, and
- a processing unit receiving the electrical signals produced by the means of detection.

According to the invention, the polarisation modulator is included in an optical component according to the invention. Moreover, the means of detection include a polarimeter which produces n measured quantities representing the polarisation states of the measurement beam, and the processing unit produces, by Fourier transform, m values for each of the n quantities measured, with n×m≧16 and m≧4, thus providing access to the sixteen coefficients of the Mueller matrix.

The Mueller ellipsometer according to the invention is therefore based upon phase modulations of a single frequency. It enables any rotating element to be surmounted, and high-frequency measurements to be made, as well as being easy to implement and providing accurate results. In addition, it can be adapted easily to the existing conventional phase-modulation ellipsometry systems, and can take advantage of the digital processing techniques which are usually employed.

The light source and the polariser should be considered as being equivalent to a linearly polarised light source.

The means of detection can include one or more photo-detectors. In the first case (single-channel technique), n=1 and m≧16 and the polarimeter includes a system for modulating the polarisation. In particular, this modulation system can be the optical component according to the invention. The light intensity detected is then dependent on time. The second case is that of a multi-channel technique, which is advantageous in particular for performing simultaneous measurement of the coefficients using only a single modulation polarisation in the PSG. The polarimeter can then separate the measurement beam into several secondary beams, each with a distinct polarisation state, and being detected by one of the photo-detectors, or can produce consecutive reflections of the measurement beam to different photo-detectors. It is preferable that the PSD or polarimeter should not introduce any new temporal modulation, since the quantities measures are linearly related to the four components of the Stokes vector.

The quantities measured are dependent on time, and are usually the intensities measured by the photo-detector(s).

It is advantageous to choose harmonics of the ω pulse, and to calculate the corresponding harmonic orders of each of the quantities measured. The values produced are then the harmonic coordinates of the quantities measured according to the fixed harmonic components. The minimum number of harmonic coordinates per measured quantity to obtain the sixteen coefficients of the Mueller matrix is 4, since a higher number of harmonic coordinates involve redundancies in the determination of these coefficients.

The product of the Mueller matrix (M), by the Stokes vector (S), of the incident beam to the sample is equal to the Stokes vector (S2) of the measurement beam emerging from the sample.

The PSG of the Mueller ellipsometer is composed of the polarisation modulator, while the PSD is composed of the means of detection. The PSG and the PSD are respectively a modulation matrix (W) and a detection matrix (A), where the latter may or may not vary with time. Since the harmonics of the ω pulse fixed for the calculation of the values produced are grouped together in a harmonic vector (H), the product of the modulation matrix (W) by the harmonic vector (H) gives the Stokes vector (S1) of the incident beam exiting from the PSG. In the multi-channel case, since the quantities measured are grouped together in a quantity vector (P), the product of the detection matrix (A) by the Stokes vector (S2) of the measurement beam sent back by the sample is equal to the quality vector (P). By indicating the dependency on time t of P and H, $$P(t)=(AMW)H(t).$$

In the presence of opto-electrical modulators producing a phase shift $\delta(t)=\omega t$, the harmonic vector H(t) is written as follows:

$$H(t) = \begin{pmatrix} \cos \omega t \\ \sin \omega t \\ \cos (2\omega t) \\ \sin (2\omega t) \end{pmatrix}$$

In the presence of photo-elastic modulators producing a phase shift $\delta(t)=A_0\sin(\omega t)$, it becomes:

$$H(t) = \begin{pmatrix} \cos (A_0\sin \omega t) \\ \sin (A_0\sin \omega t) \\ \cos (2A_0\sin \omega t) \\ \sin (2A_0\sin \omega t) \end{pmatrix}$$

where $A_0$ is a constant set by the (modulation amplitude) photo-elastic modulator(s).

Preferably, $A_0=2.791$. For this value, the components of the harmonic vector (H)(t) are the most independent.

When the number of components for each of the quantities measured is equal to m, then the dimensions of the W, M and A matrices are respectively 4×m, 4×4 and n×4.

In the single channel case (n=1), the PSG and the PSD can correspond to any one of the realisation methods described previously, with the PSD modulating the polarisation at a frequency which is 5 times higher or lower than that of the PSG.

Since the ellipsometer is a Mueller one, then the modulation matrix (W) is necessarily of rank 4 ($W^{-1}W$ reversible), and the PSG is then said to be full. The detection matrix (A) must also be of rank 4 in the case where it is invariant in time.

Preferably n≧4, and the polarimeter does not introduce any new temporal modulation.

We thus get over the modulations in the PSD, the detection matrix (A) then being invariant over time and of rank 4. In this way, the ellipsometer provides great simplicity of use, and the high frequency capabilities (no mobile elements) allow full advantage to be taken of the existing multi-channel techniques. This is particularly effective and easy to implement.

In an advantageous form of this preferred realisation, n=4 and m=4, and the polarimeter separates the four polarisation states of the measurement beam associated with the four quantities measured.

This advantageous form corresponds to the minimal configuration, introducing no modulations in the output.

Since the ellipsometer has an optical component according to the invention in the PSG, the four values produced by Fourier transform for each quantity measured dependent on time t are then advantageously the harmonic components of this measured quantity in the base:

cos ωt, sin ωt, cos 2ωt, sin 2ωt.

Therefore keep harmonics of order 1 and 2 are kept with no need to keep the harmonic of order 0, since the mean intensity is modulated.

In a preferred manner, since m calculation harmonic components $H_\lambda(t)$ dependent on time t are grouped together in a harmonic vector H(t), then the processing unit produces the m values for each of the n quantities measured $I_h(t)$ by means of a special Fourier transform according to which the interval [0, 2π/ω] being split into in 2N discrete equally-distributed points ($T_k$), and the measured quantity $I_h(t)$ being calculated at sampling instants $t_k$, for k varying from 0 to 2N−1, the processing unit evaluates the j-th harmonic component $B_{hj}$ of the function $I_h$ for j varying from 1 to m and h varying from 1 to n by:

$$B_{hj} = \frac{1}{2N} \sum_{k=0}^{2N-1} I_h(t_k) g_j(T_k)$$

The functions $g_j(t)$ being demodulation functions chosen such that the demodulation matrix (D) given by:

$$D_{lj} = \frac{1}{2N} \sum_{k=0}^{2N-1} H_l(t_k) g_j(T_k)$$

for λ and j varying from 1 to m, is of rank ≧4.

Thus the product of B by inversion of D is used to obtain the AMW matrix directly, then to extract the Mueller matrix (M). This special fast Fourier transform or SFFT avoids the problems of singularities posed by the absence of a photo-elastic modulator, and in general can lead to an improvement in the accuracy of the results.

In a first form of the SFFT, denoted SFFT1, since the two phase modulations applied by the PSG have the same phase shift δ(t), $$\delta(t_k) = \omega T_k$$
$$g_j(T_k) = \exp(-ij\omega T_k)$$

with $1^2 = -1$.

Thus, in this SFFT1, the sampling points $t_k$ are not equally-distributed, so that the measurements have to be triggered in each period at precise predetermined instants. In relation to a conventional FFT, the SFFT1 therefore requires an adaptation of the hardware elements of the processing unit, but the same software can be retained.

The SFFT1 allows a phase shift δ(t) to be obtained which is equal to ωt (mod 2π) over a period, irrespective of the phase modulators employed. It gives very accurate result while also avoiding the appearance of singularities.

In a second form of the SFFT, denoted SFFT2, $T_k = T_k$, and $g_j$ such that D is the identity matrix.

The demodulation functions $g_j(t)$ thus constitute the dual base of the calculation harmonic coordinates $h_\lambda(t)$. The nature of the $g_j$ functions therefore differ according to whether the polarisation modulator contains opto-electrical or photo-elastic modulators.

The SFFT2 allows the hardware to be kept unchanged in relation to a conventional FFT, because of the fact that the sampling points $t_k$ are equally-distributed. On the other hand, it requires that the software of the processing unit be changed.

The demodulation obtained with the SFFT2 gives a minimal signal to noise ratio and crosstalk.

The means of detection and the processing unit are adapted with advantage for spectroscopic measurements.

The invention also covers a process for calibrating the ellipsometer according to the invention. The polariser and the polarisation modulator constitute a polarisation states generator, and since the means of detection respectively have a modulation matrix and a detection matrix:

a set of calibration identities is chosen which have known Mueller matrices, one of these entities being the identity matrix.

for each of the calibration entities, this entity is adopted as a sample in the ellipsometer, an incident light beam is entitled which is polarised linearly with the light source and the polariser, the incident beam is modulated with the coupled modulator, the modulated incident beam is sent to the entity and a measurement beam is returned, measured quantities are produced by the means of detection and the values by the processing unit, and using these values, a measured matrix is constructed which is a product of the detection matrix, the Mueller matrix of the entity, and the modulation matrix.

a system of linear equations is established from the measured matrices, and this system is solved in order to extract the modulation and detection matrices.

Performing a measurement with the entity corresponding to the identity matrix means that no sample should be put between the PSG and the PSD.

Measurement of the modulation matrices W and detection matrices A is thus effected automatically by means of this self-calibration process. Accurate results are obtained in a rapid and simple manner, and in particular without having to disassemble the device.

In an advantageous implementation of the calibration process according to the invention, a set of entities is chosen which includes:

a linear polariser at 0° on transmission, a linear polariser at 45° on transmission, and a partial polariser and phase shifter without singular values.

This calibration process is particularly appropriate in the case where the PSD separates the measurement beam into four polarisation states (n=4) and where four values are determined corresponding to the first harmonics, for each of the associated detected intensities.

The invention also concerns a Mueller ellipsometric measurement process intended for measurement of a sample represented by the coefficients of a Mueller matrix. In this process:

a linearly polarised incident light beam is emitted the incident beam is modulated with a polarisation modulator, the modulated incident beam is sent to the sample, and a measurement beam is returned the measurement beam is detected and electrical signals are produced by the means of detection, and the electrical signals are transmitted to a processing unit.

According to the invention:

two successive phase modulations are applied to the incident beam by means of a polarisation modulator, the two modulations being strictly at the same frequency of ω/2π, and being coupled by a system which modifies the polarisation state of the light between the two modulations.

n measured quantities are produced representing the polarisation states of the measurement beam using the means of detection.

using Fourier transform, m values are produced for each of the n measured quantities by means of the the processing unit, with n×m≧16 and m≧4, allowing access to the sixteen coefficients of the Mueller matrix.

This process is used to measure the complete Mueller matrix at high frequency, accurately and in a simple manner.

The demodulation can be achieved using a standard fast Fourier transform (FFT) or using the SFFT. The latter improves accuracy in the presence of opto-electrical modulators, and makes possible calculation of the m values in the presence of photo-elastic modulators.

BRIEF DESCRIPTION OF THE DRAWINGS

This present invention will be illustrated by the following description using examples of realisation of the optical component, of the polarimeter, of the Mueller ellipsometer according to the invention, and of the implementation of the calibration process and the ellipsometric measurement process according to the invention, provided here as a guide only and not exhaustive in any way, with reference to the drawings.

DETAILED DESCRIPTION OF PREFERRED EMBODIMENT

Figure 1:
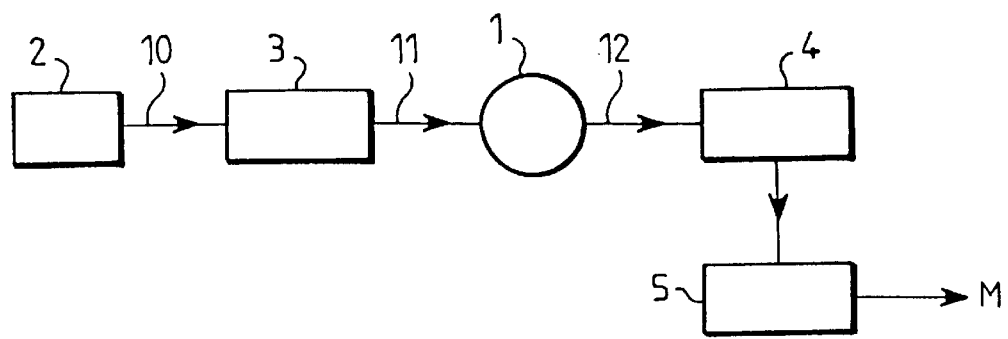
FIG. 1 is a diagram of principle, showing the Mueller ellipsometer according to the invention.

A Mueller ellipsometer according to the invention, represented in FIG. 1, is made up of a light source (2) emitting an incident beam (10) and a polarisation states generator or PSG (3), which transforms, in a controlled manner, the polarisation state of the incident beam (10). The PSG (3) linearly polarises the incident beam (10) and applies a polarisation modulation to it. It transmits the modulated incident beam (11) to a sample (1) to be measured. The ellipsometer also includes a polarisation states detector or PSD (4) which detects a measurement beam (12) returned by the sample (1), and a processing unit (5) which receives the electrical signals produced by the PSD (4). Since the sample (1) has a Mueller matrix (M), the processing unit (5) fully determines this matrix (M) automatically in the course of a measurement.

Figure 2:
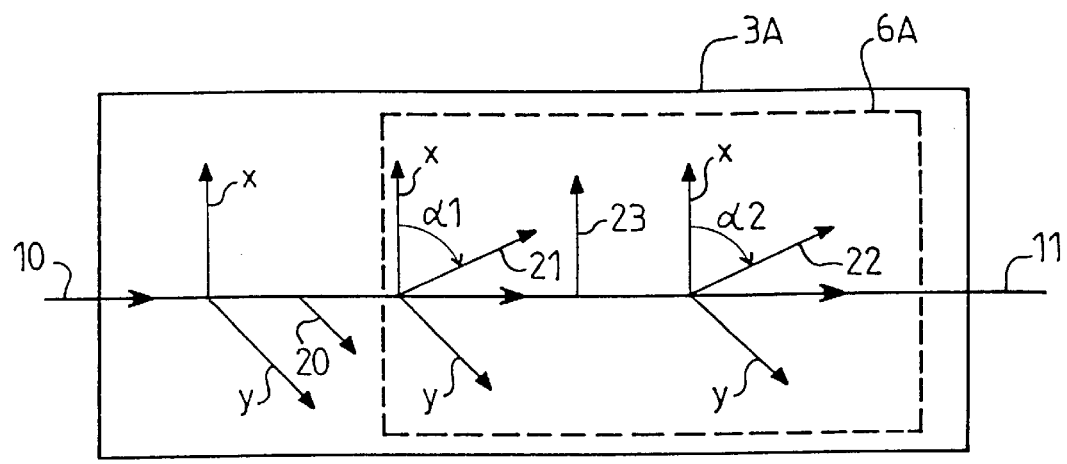
FIG. 2 represents the PSG in a first method of realisation of the Mueller ellipsometer according to the invention.

In a first method of realisation of the Mueller ellipsometer according to the invention, illustrated in FIG. 2, the PSG (3A) includes a linear polariser (20) and a coupled modulator (6A), made up from two phase modulators (21 & 22) and a coupling system (23) of the partial polariser and phase shifter type. The two phase modulators (21 & 22) have the same orientation, and the coupling system (23) in interposed between them, sending the incident beam (10) of the first phase modulator (21) to the second phase modulator (22).

Preferably, the orientations of the various elements are as follows. Since the incident beam (10) has a direction and sense of propagation and an incident plane defined from this propagation direction and from sample 1, a reference is formed comprising a first axis (x) which is perpendicular to the direction of propagation and in the incident plane, a second axis (y) perpendicular to the incident plane, and a third axis parallel to the direction of propagation and oriented in the same sense, this reference being direct. The polariser (20) is then a perfect polariser oriented on the y axis. The two phase modulators (21 & 22) are identical and oriented in the x-y plane in accordance with directions respectively forming angles $\alpha_1$ and $\alpha_2$ with the y axis. Angles $\alpha_1$ and $\alpha_2$ are best to be identical, and preferably equal to $\pi/4$. The coupling system (23) is oriented on the x axis.

In operation, the incident beam (10) is linearly polarised by the polariser (20), and then undergoes a coupled double modulation, because of the phase modulators (21 & 22) and the coupling system (23). The coupling system (23) performs two functions—a partial polarisation (imperfect polariser) which modulates the average intensity (I), and a phase shift which combines the U and V components of the Stokes vector (S).

Figure 3:
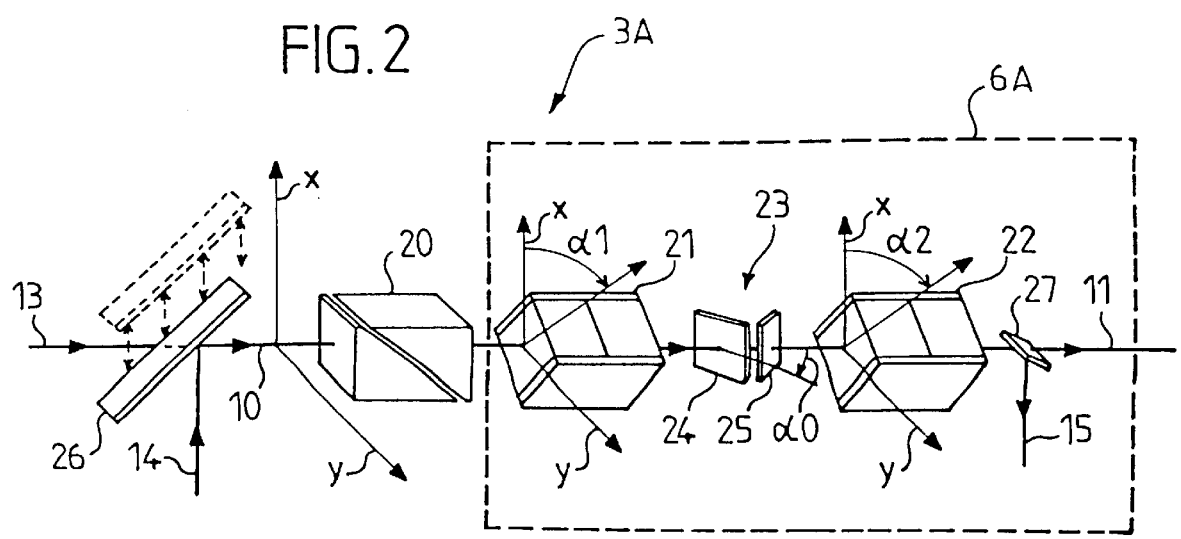
FIG. 3 shows an arrangement corresponding to the PSG of FIG. 2.

According to a particular realisation of this PSG (3A), represented in FIG. 3, the polariser (20) is a polariser marketed under the name "Glan Thomson Polariser", and the phase modulators (21 & 22) are opto-electrical modulators of the Pockels cell type. The use of opto-electrical modulators renders possible an absolute phase control which can be used to synchronise phase modulators (21 & 22). The double modulator (6A) also includes cells marketed under the name of Peltier cells, thermally regulating the Pockels cells.

The coupling system (23) is best if it includes two transparent blades (24 & 25) covered with a very thin layer of gold, oriented to avoid generation of a beam shift. It receives the incident beam (10) with an incidence angle preferably equal to 60°, linked to $\alpha_0$ (the angle between the direction of propagation and the orientation of the first blade (24)).

The coupling system (23) on transmission can be replaced by a reflection coupling system, in the form of a chrome mirror for example.

PSG 3A also includes a beam separator (27), placed on the trajectory of the modulated incident beam (11) after phase modulators (21 & 22). This beam separator (27) taps off a control beam (15), used to act upon the modulations in order to compensate for parasitic fluctuations. It is preferable that the separator (27) should tap off 4% of the light intensity in the control beam (15). This can be a glass blade inclined at 45° to the direction of propagation.

The light source (2) advantageously emits laser beams (13 & 14) at several wavelengths. The ellipsometer then includes a mobile mirror (26) used to select the wanted wavelength.

Figure 4:
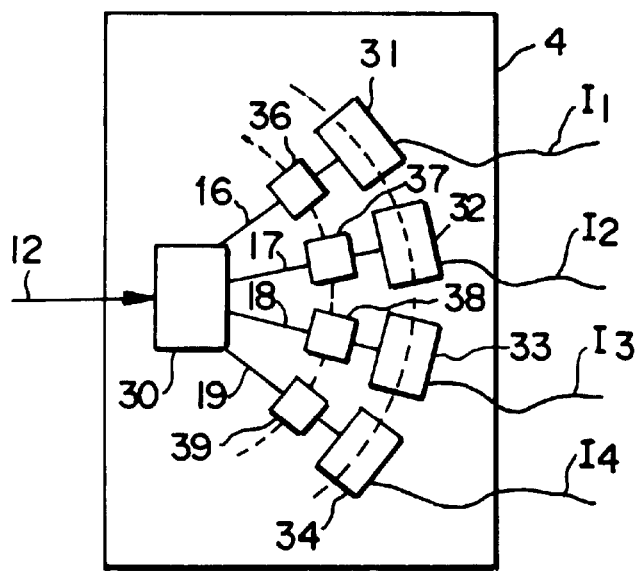
FIG. 4 represents the PSD of the first method of realisation of the Mueller ellipsometer.

The PSD (4), as represented in FIG. 4, advantageously a beam separator (30) separating the measuring beam (12) into at least four secondary beams (16–19). The PSD (4) also includes polarisation analysers (36–39), giving to each of these secondary beams (16–19) a distinct polarisation state and photo-detectors (31–34), respectively detecting intensities $I_1$ and $I_4$ of secondary beams (16–19). As an example, since secondary beams (16–19) are four in number, the associated polarisation analysers (36–39) are respectively nothing, a linear polariser at 90°, a linear polariser at 45°, and the combination of a quarter-wave blade and a polariser at 90°.

The control and treatment arrangement for the signal will now be described in detail, making reference to FIG. 5.

The PSG (3A) includes a signal generator (41) connected to two modulators (21 & 22) by means of an amplifier (42). This signal generator (41) applies a voltage to modulators (21 & 22) via the amplifier (42). This voltage causes a phase shift δ in the polarisation on the beam (10), which is proportional to this voltage over time t. Preferably, this phase shift δ is composed of ramps with a period of 2π/ω and a slope of ω in each period. In this way, and periodic function of δ(t) with a period of 2π is the same periodic function of ωt.

Processing unit (5) includes a data signal processor or DSP (40) which receives electrical signals from the PSD (4). The PSD (4) can be connected to the DSP (40) by a multiplexer (47) or by any other known means. The DSP (40) calculates the wanted harmonic coordinates of the intensities of the measured secondary beams (16–19). The calculation harmonics are advantageously the four of order 1 and 2:

$$\cos \omega T, \sin \omega t, \cos 2\omega t, \sin 2\omega t.$$

It is not necessary to retain the continuous component, since the mean intensity of the incident beam (10) is modulated by the PSG (3A).

In a realisation variant, the DSP (40) calculates the harmonic coordinates in a base consisting of more than four harmonics, grouping together the preceding and the harmonics of order greater than 2.

The DSP (40) is equipped with an analogue-digital converter (ADC) which provides it with the values of the electrical signals from the PSD (4) at the sampling points, as well as a memory of the FIFO type, which averages these values over several periods before they are processed by the DSP (40). Sampling can include sixteen points per period, for example.

The processing unit (5) also includes a computer (43), which receives the harmonic components calculated by the DSP (40).

Figure 5:
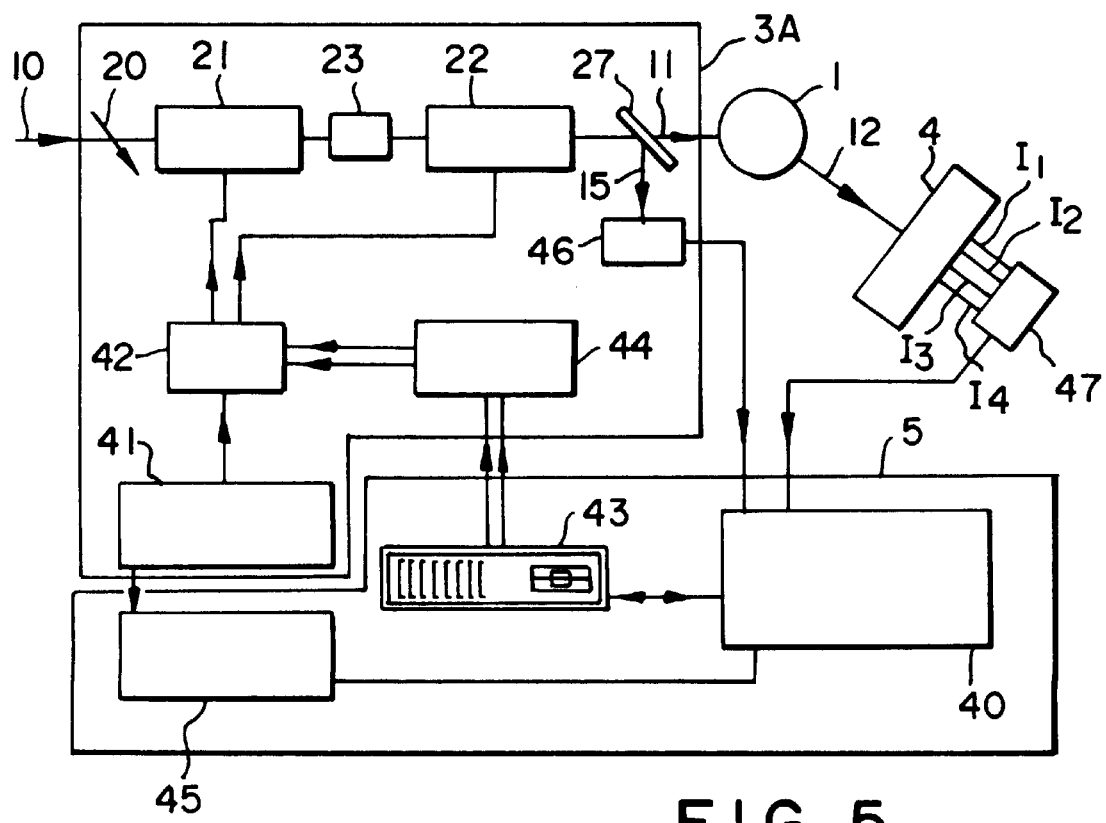
FIG. 5 represents all of the Mueller ellipsometer according to the first method of realisation in FIGS. 2 to 4, highlighting the control and processing systems.

In a preferred manner, as illustrated in FIG. 5, the processing unit (5) includes a sampling generator (45) which is phase-slaved to the signal generator (41). The sampling generator (45) supplies the sampling instants to the DSP (40). Signal processing by the DSP (40) from these instants is advantageously implemented by a special fast Fourier transform or SFFT, the principle of which is described below in a first method of implementation—the SFFT1. Since interval (0, 2π/ω) is split into $T_k$ equally-distributed discrete points, then the sampling generator (45) determines the sampling instants $t_k$ for each period, given by:

$$\delta(t_k) = \omega T_k$$

for k varying from 0 to 2N–1. Since an electrical signal supplied by the PSD (4) is represented by a function (f) of time (t), then the DSP (40) evaluates the j-th harmonic component $B_j$ of the function f by:

$$b_j = \frac{1}{2N} \sum_{k=0}^{2N-1} f(t_k) \exp(-ij\omega T_k)$$

The usual case of the FFT corresponds to $t_k = T_k$, irrespective of the value of k.

The advantage of the SFT is that it allows digital correction of the disparities in the phase shift δ actually applied by the phase modulators (21 & 22) in relation to the ideal phase shifts which would result in perfect ramps. These disparities can, for example, be due to the rise time in the amplifier (42), leading to errors of the order of 10% at 50 kHz in the theoretical form of the modulation matrix (W), but have no effect on the accuracy of measurement M. Since this disparity increases with frequency, then the SFFT allows constant performance to be achieved at the highest frequencies.

Figure 6:
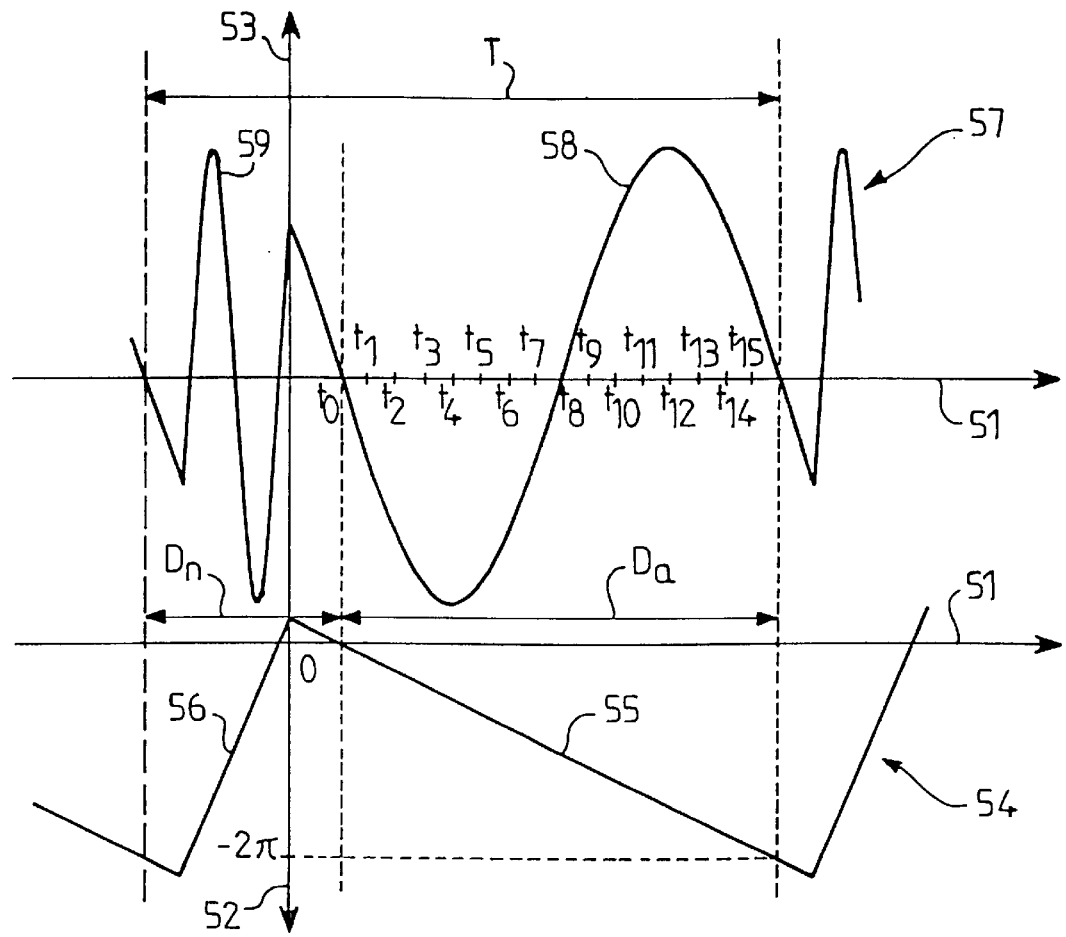
FIG. 6 represents a temporal evolution of the phase shifting and an acquisition sampling used in the arrangement in FIG. 5.

Thus, as can be seen on FIG. 6, the graph (54) giving the phase shift δ (axis 52) as a function of time t (axis 51) allows a linear part (55) corresponding to the wanted ramp and a parasitic part (56) due to the rise time, in each modulation period T. The sampling generator (45) operates in such a way that the sampling instants, $t_0, t_1 \ldots T_{15}$ are equally-distributed over an acquisition period $D_a$ associated with the linear part (55). On the other hand, no acquisition takes place during a non-acquisition period $D_n$, corresponding to the parasitic part (56). A sinusoidal variation of the phase shift δ (axis 53) as a function of time (axis 51) therefore has a curve (57) which allows a regular part (58) for a time $D_a$ and a parasitic part (59) for the period $D_n$, in each period T. The regular part (58) is that which would be obtained with a phase shift of ωt (plus or minus). The modulation form producing the curve (54) is normally achievable only with phase modulators of the opto-electrical type.

This signal processing is particularly effective and accurate. In a variant however, the sampling generator (45) is absent from the processing unit (5), and the DSP (40) is fitted with a phase locked loop or PLL. In this case, the PLL generates sampling instants $T_k$, equally-distributed in each period, and the DSP (40) effects a normal fast Fourier transform.

In a second method of implementation of the SFFT, denoted SFFT2, the sampling generator (45) is absent from the processing unit (5), and the DSP (40) is fitted with a PLL which generates 2N sampling instants $T_k$, equally-distributed in each period. However instead of the DSP (40) effecting a normal fast Fourier transform as in the previous case, it proceeds in the following way. The computer (43) first stores in memory m predetermined functions $g_j(t)$, known as modulation functions. The $g_j$ functions form a dual base of m calculation harmonic coordinates $H_\lambda(t)$, grouped together in a harmonic vector H(t). When the phase modulators (21 & 22) are opto-electrical, H(t) is (with m=4):

$$H(t) = \begin{pmatrix} \cos \omega t \\ \sin \omega t \\ \cos(2\omega t) \\ \sin(2\omega t) \end{pmatrix}$$

and when the phase modulators (21 & 22) are photo-elastic, it is then (where A° is a constant)

$$H(t) = \begin{pmatrix} \cos(A_0 \sin \omega t) \\ \sin(A_0 \sin \omega t) \\ \cos(2A_0 \sin \omega t) \\ \sin(2A_0 \sin \omega t) \end{pmatrix}$$

With the sampling of the $T_k$, we then get:

$$\frac{1}{2N} \sum_{k=0}^{2N-1} H_l(T_k) g_j(T_k) = \begin{cases} 1 & \text{if } j = l \\ 0 & \text{if } j \neq l \end{cases}$$

The DSP (40) then evaluates the j-th harmonic component $b_j$ of a function f (representing an electrical signal supplied by the PSD (4)), by:

$$b_j = \frac{1}{2N} \sum_{k=0}^{2N-1} f(T_k)g_j(T_k)$$

The PSG (3A) is equipped with a phase modulation temporal stabilisation system. This system (FIG. 5) includes the separator (27), which sends the control beam (15) to the DSP (40) by means of a photomultiplier (46). The phase modulation temporal stabilisation system also includes a digital-analogue converter (44) which receives control signals from the computer (43), and supplies the amplifier (42) with control voltages (low voltages) $U_1$ and $U_2$, respectively intended for the phase modulators (21 & 22).

In operation, the DSP (40) calculates the harmonic components associated with the control beam (15), representing the modulated incident beam (11) in the fixed harmonic base. It supplies these harmonic coordinates to the computer (43), which determines, from setpoint values, the voltage $U_1$ and $U_2$ to be applied, to compensate for the parasitic phase shifts, due in particular to temperature variations. The computer (43) then supplies these voltages ($U_1$ and $U_2$), to the amplifier (42) by means of a DAC (44). Each of these control voltages ($U_1$ and $U_2$) is then added to the voltage U supplied by the function generator (41), before amplification by the amplifier (42).

Figure 7:
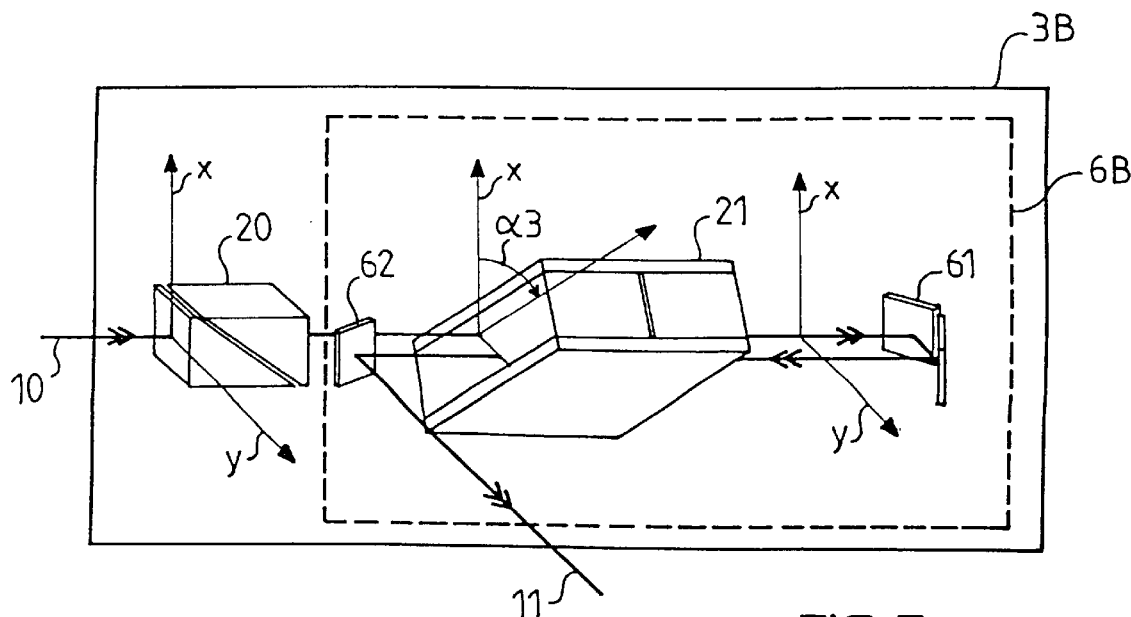
FIG. 7 shows the PSG of a second method of realisation of the Mueller ellipsometer according to the invention.

In a second method of realisation of the ellipsometer according to the invention, represented in FIG. 7, the PSG (3B) has only a single phase modulator. In this second method of realisation, identical elements to those in the first method of realisation are designated by the same references. The PSG (3B) includes a polariser (20) which linearly polarises the incident beam (10), and a coupled modulator (6B) which includes a single phase modulator (21) and a coupling system (61) of the partial polariser and phase shifter type, operating by reflection. The phase modulator (21) is interposed between the polariser (20) and the coupling system (61) so that it produces a first modulation of the polarised incident beam (10), and sends it to the coupling system (61), the latter returning the incident beam (10) to the phase modulator (21) which produces a second modulation. The coupled modulator (6B) also includes a mirror (62) placed between the polariser (20) and the phase modulator (21), which reflects the twice-modulated incident beam (11) toward the sample (1).

Since axes x and y are defined as in the first method of realisation, according to a preferred form, the polariser (20) is oriented on the y axis and the modulator (21) is oriented in the x-y plane in a direction forming an angle $\alpha_3$ with the x axis, where $\alpha_3$ is equal to 45°. For its part, the coupling system (61) is oriented on the x axis, in a manner which allows a return of the incident beam (10) parallel to its incident trajectory. The mirror (62) advantageously returns the modulated incident beam (11) along the y axis.

In a first variant of realisation, the phase modulator (21) is an opto-electrical modulator (Pockels cell). Such a modulator (21) allows external phase-shift control, and a pass band in excess of 100 MHz. This pass band is dependent only on the signal generator (41) and the amplifier (42).

Figure 8:
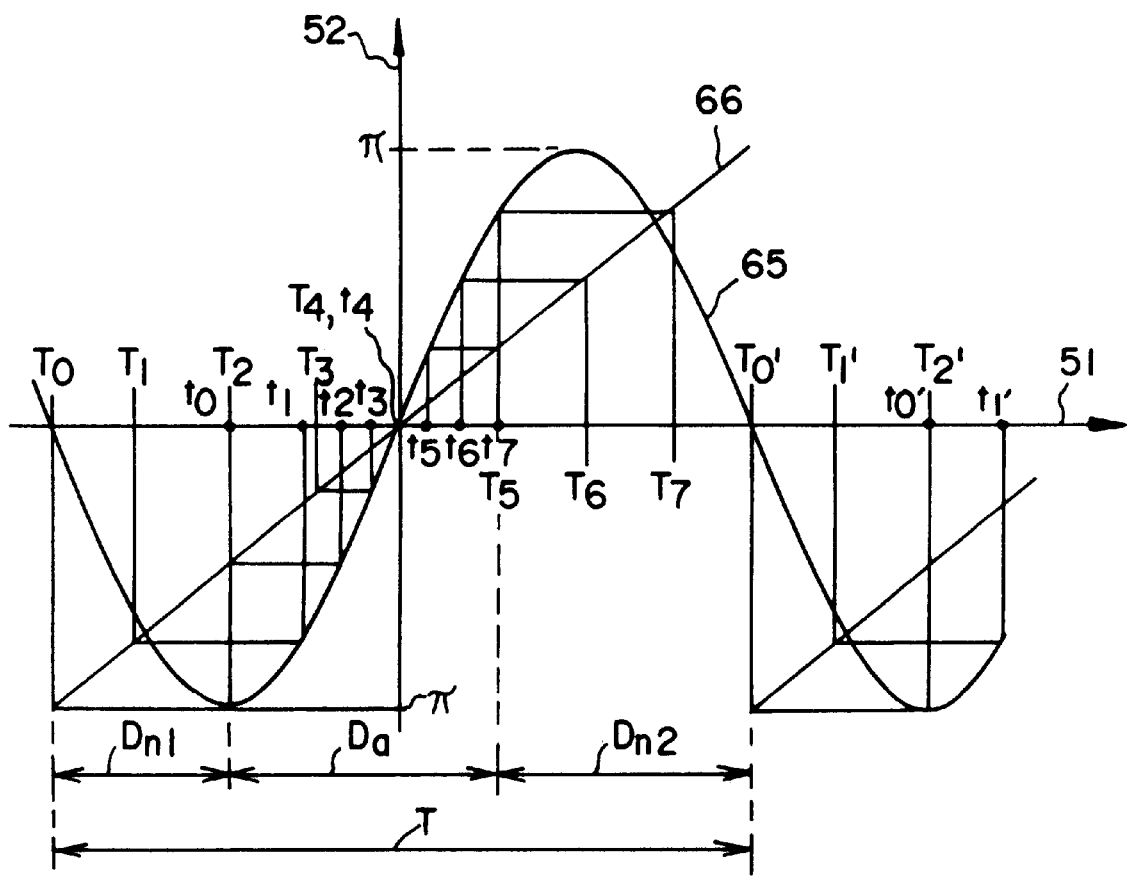
FIG. 8 represents a temporal evolution of the phase shifting and an acquisition sampling used with the second method of realisation of the ellipsometer in FIG. 7.

In a second variant of realisation, the phase modulator (21) is a photo-elastic modulator. An extended range of wavelengths and a large optical window are thus obtained. The form of phase shift is then fixed, and is proportional to $\sin \omega t$ (FIG. 8). In this second variant of realisation, the wanted harmonics are calculated by means of the previously described SFFT, by a sampling generator and a DSP, for example, similar to those of the first method of realisation, respectively referenced as 44 and 45, and the SFFT1 (FIG. 5). The modulation matrix (W) of the PSG (3B) is therefore of rank 4, while a normal FFT would render this matrix singular. The phase modulator (21) has a modulation amplitude greater than or equal to π, in order to render SFFT1 applicable.

As an example, the phase modulator (21) applies a temporal phase shift δ of the form:

$$\delta(t) = \pi \sin \omega t$$

as represented in Figure eight. By adopting a sampling of 8 points per period T, equal to $2\pi/\omega$, the eight points $T_0$–$T_7$ are obtained equally-distributed over period T (and in a similar manner over the following period, $T'_0$–$T'_7$). The eight sampling instants $t'_0$ to $t'_7$ (and over the following period $t'_0$, $t'_1$, etc.) are obtained with the formula of the SFFT1, and distributed over an acquisition period $D_a$. The complementary period in period T is composed of two non-acquisition periods, $D_{n1}$ and $D_{n2}$. The images of the sampling instants ($t_k$) are then obtained from the curve (65) giving the phase shift (δ) as a function of time (t) and of curve 66, of the form $\omega t$. The images of the instants ($t_k$) on curve 65 correspond to the images of points $t_k$ on curve 66.

The choice of the harmonic base in this second method of realisation is advantageously the same as that indicated for the first method of realisation.

SFFT2 provides another advantageous implementation.

Figure 9:
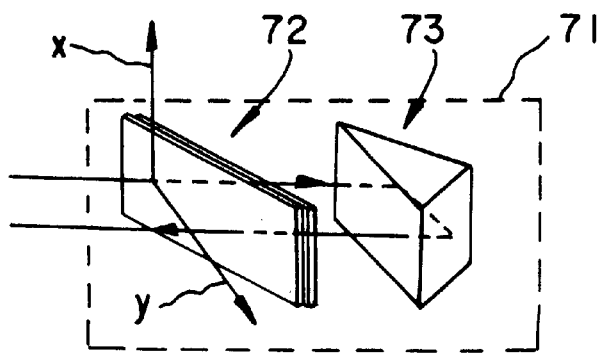
FIG. 9 represents form of realisation of the PPS other than that of FIG. 7.

In another form of realisation of the coupling system on reflection, referenced 71, and represented in FIG. 9, the PPS includes two distinct elements (72 and 73) respectively realising the partial polarisation functions on the one hand, and the phase shifting and reflection functions on the other.

The partial polarisation element 72 is advantageously composed of a stack of air-material blades formed by successive glass plates of index N1. This is preferably oriented on the Brewster angle. This provides the best compromise between the partial polarisation and the total intensity part, without phase shift. The type of materials used and the number of blades used are chosen in accordance with the spectral range to be covered.

The phase-shift and reflection element is a prism. An incident beam on this element (73) is thus reflected, with a phase shift which depends on the index N2 of the prism, without undergoing partial polarisation and without losing its intensity. Preferably element 73 is a straight prism, so that the incident beam is reflected in parallel.

The optimum values of the N1 and N2 indices are given by the following formulae, in which ni designates the number of passages across the air-glass blades of element 72 (counted in both directions), at the Brewster incidence:

$$N1 = (tg 65.90°)^{1/(2ni)} + \sqrt{(tg(65.90°)^{1/ni-1})}$$

$$N2 = 1.703$$

Thus optimum conditioning of the modulation matrix (W) is thus obtained.

As an example, element 73 is a glass prism of the type marketed under the name C4834, which has indices of 1.68 at 404 nm and 1.64 at 706 nm.

As far as element 72 is concerned, the number of passages (n) is chosen according to the range of application in wavelength, and gives the N1 index.

In a first example, with applications in the infra-red, element 72 has a single glass blade which is traversed once only, either go or return (ni=1). The optimum value of N1 is then 2.6, which can be approached by ZnS, for instance.

In a second example, element 72 has one glass blade which is traversed on go and return (ni=2), with N1=1.927.

In a third example, with applications in the visible spectrum, element 72 has two glass blades (ni=4) and N1=1.578. The plates are then composed of the material marketed under the name of BK7, for instance.

In a fourth example, with applications in the ultra-violet and the visible, element 72 has three glass plates (ni=6) and N=1.448. The plates are then in cast silica, for instance.

In the methods of realisation presented up to now, the PSD (4) is based on a polarisation state separator (FIG. 4) which includes fixed elements without modulation. A variant consists of using the consecutive reflections of the measurement beam (12) on at least 12 photo-detectors. A description of such a PSD can be found in "Arrangement of four photo-detectors for measuring the state of polarisation of light", R. M. Azzam, Optics Letters, vol 10, pp. 309–311, 1985. These multi-channel techniques have as their common point measurement of the polarisation states without either polarisation or moving parts.

In another method of realisation, the PSD (4) includes a polarisation modulator at a frequency other than that of the PSG (3). The ellipsometer then uses a single-channel technique, and the harmonic base chosen includes at least sixteen components. It is also possible to use a single channel technique for the PSD, or a multi-channel technique involving mobile elements.

In the single-channel case, (n=1), one of the PSGs (3A, 3B), described previously, can be used as the PSD in the output arm, associated with any of the PSGs in the input arm. In this case, the PSD corresponds to FIGS. 2 to 7, except that the polariser (20) is located in the emergent beam (11) instead of the incident beam (10). The orientation of the optical elements is advantageously the same in the PSD and the PSG. The modulation frequency of the PSD is 5 times or $\frac{1}{5}$th of that ($\omega/2\pi$) of the PSG. The processing unit supplies 16 independent values (m=16) by Fourier transform.

More generally, any one of the PSGs (3A, 3B) can be used independently as a polarisation states detector (measurement of the Stokes vector) in any optical arrangements.

Are two levels of calibration of the ellipsometer.

The first level concerns orientation of the optical elements, determination of the modulation amplitude and the control operation. Operation is preferably as follows: an absolute reference angle is specified by orientation of the polariser (20) of the PSG (3). To do this, a linearly polarised light is arranged in the incident plane to be reflected without any cross polarisation. Thus a polariser is used in the incident beam and one, turned at $\pi/2$ from the first, in the reflected beam, and these are turned together until the beam is completely extinguished. The other optical elements are then aligned in relation to the polariser (20).

In order to orient the phase modulators (21 & 22), the modulation is cancelled, corresponding to alignment of the input polariser (20) and the fast axis of the modulators.

The correct modulation amplitude, is obtained that is the correct slopes for the ramps ($\delta(t)=\omega t$), minimising the high harmonics in relation to the harmonic of order 1, using a single modulator. The parameters necessary for control are determined experimentally.

The second calibration level, which is the more important, is determination of the modulation matrices (W) and the detection matrices (A). Preferably, a self-calibration process, is employed as described below. A set of calibration entities having known Mueller matrices is chosen. One of these Mueller matrices is the identity matrix $I_0$ (nothing on transmission). Then successively each of the other calibration entities is adopted as sample 1, and the ellipsometric measurements are performed. For each Mueller matrix (M) entity, the AMW matrix is obtained from these measurements. The $AI_0W$ matrix is also measured. A system of linear equations is established and solved these in such a way as to extract the modulation matrices (M) and the detection matrices (A).

Preferably, a sufficient number of entities is chosen to over-determine the W and A matrices. As an example, since the PSD (4) includes a polarisation state separator which does not introduce any new temporal modulation, four entities successively are used. One of these four entities is the vacuum, the measurement being performed on transmission without a sample. All of the other three entities include a linear polariser at 0° on transmission, a linear polariser at 45°, and a partial polariser and phase shifter without a singular value on reflection or transmission. The latter can be a quarter-wave blade. Preferably, its Mueller matrix can be measured exactly, using a standard ellipsometer.

The W and A matrices are extracted from the over-determined linear system by means of a least-squares algorithm.

This self-calibration method gives very accurate results, because of the fact that it is related to the self-coherency of the Mueller formalism. It is also easy and quick to implement.

The Mueller ellipsometer according to the invention is appropriate for both monochromatic and spectro-chromatic measurements.

What is claimed is:

1. An optical device for polarization modulation including a polarization modulator which modulates an incident beam of linearly polarised light including all four components of a Stokes vector thereof, and returns a modulated incident beam, the polarization modulator being a coupled modulator modulating the incident beam twice in succession, the two modulations being strictly at the same frequency of $\omega/2\pi$ and having the same orientation, and a coupling system coupling the modulations and modifying a polarization state of the light between the two modulations.

2. An optical device according to claim 1, wherein the coupled modulator includes a phase modulator producing the two successive modulations, and the coupling system includes a partial polarizer and a phase shifter, the phase modulator producing the first modulation and sending the incident beam to the coupling system, with the coupling system returning the incident beam to the phase modulator and the phase modulator producing the second modulation.

3. An optical device according to claim 2, wherein the light of the incident beam is polarised linearly in one direction of polarization (y), and the phase modulator and the coupling system are respectively oriented at 45° and 90° from the direction of polarization (y).

4. An optical device according to claim 1, wherein the coupled modulator includes two phase modulators, respectively producing the two successive modulations, the two phase modulators having a single orientation, and the coupling system includes a partial polarizer and a phase shifter, said coupling system being interposed between the two phase modulators, and sending the incident beam of the first to the second of said phase modulators.

5. An optical device according to claim 4, wherein the light of the incident beam is polarised linearly in one direction of polarization (y), and the phase modulators and the coupling system are respectively oriented at 45° and 90° from the direction of polarization (y).

6. An optical device according to claim 1, wherein the coupling system functions on reflection, and includes a first partial polarization element and a second phase-shift and detection element.

7. An optical device according to claim 6, wherein the first partial polarization element is made up from a stack of air-material interfaces at the Brewster angle, and the second phase-shift and detection element is composed of a prism.

8. A polarimeter, it includes an optical device for polarization modulation including a polarization modulator which modulates an incident beam of linearly polarised light including all four components of a Stokes vector thereof, and returns a modulated incident beam, the polarization modulator being a coupled modulator modulating the incident beam twice in succession, the two modulations being strictly at the same frequency of $\omega/2\pi$ and having the same orientation, and a coupling system coupling the modulations and modifying a polarization state of the light between the two modulations.

9. A Mueller ellipsometer intended for measurement of a sample represented by the coefficients of a Mueller matrix (M), including:

a light source emitting an incident light beam, a polarizer, linearly polarising said incident beam, a polarization modulator modulating said incident beam, said sample receiving the modulated incident beam and returning a measurement beam, means to detect the measurement beam, producing electrical signals, and a processing unit receiving the electrical signals produced by the means of detection, wherein the polarization modulator is included in an optical component, the polarization modulator being a coupled modulator modulating the incident beam twice in succession, the two modulations being strictly at the same frequency of $\omega/2\pi$, and a coupling system coupling the modulations and modifying a polarization state of the light between the two modulations, so that the means of detection include a polarimeter producing n measured quantities ($I_1$–$I_n$) representing the polarization states of the measurement beam, and so that the processing unit produces, by Fourier transform, m values for each of the n measured quantities ($I_1$–$I_n$), with m being the number of components of each of the quantities measured, with n×m≦16 and m≧4 providing simultaneous access to the sixteen coefficients of the Mueller matrix (M).

10. An ellipsometer according to claim 9, wherein n≧4 and so that the polarimeter does not introduce any new temporal modulation.

11. An ellipsometer according to claim 10, wherein n=4 and m=4, and so that the polarimeter separates the four polarization states of the measurement beam associated with said four measured quantities ($I_1$–$I_4$).

12. An ellipsometer according to claim 11, wherein the four values produced by Fourier transform for each measured quantity ($I_1$–$I_4$), dependent on time (t), are the harmonic components of said measured quantity ($I_1$–$I_4$), in the base:

$$\cos \omega t, \sin \omega t, \cos 2\omega t, \sin 2\omega t.$$

13. An ellipsometer according to claim 9, wherein m harmonic calculation coordinates $H\lambda(t)$, dependent on time (t) being grouped together in harmonic vector H(t), the processing unit produces the m values for each of the n measured quantities ($I_h(t)$) by means of a special Fourier transform, according to which the period (0, $2\pi/\omega$) being split into 2N equally-distributed discrete points ($T_k$), and the measured quantity ($I_h(t)$) being calculated at sampling instants $t_k$, for k varying from 0 to 2N−1, the processing unit evaluates the j-th harmonic component $B_{hj}$ of the function $I_h$ for j varying from 1 to m, and h varying from 1 to n, by:

$$D_{lj} = \frac{1}{2N} \sum_{k=0}^{2N-1} H_l(t_k) g_j(T_k)$$

the functions $g_j(t)$ being demodulation functions such that the demodulation matrix D given by:

$$B_{hj} = \frac{1}{2N} \sum_{k=0}^{2N-1} I_h(t_k) g_j(T_k)$$

for $\lambda$ and j varying from 1 to m is of a rank equal to 4 or above.

14. An ellipsometer according to claim 13, wherein with the two phase modulations applied having the same phase shift ($\delta(t)$), the values chosen are:

$$\delta(t_k) = \omega T_k,$$

and $$g_j(T_k) = \exp(-ij\omega T_k)$$

with $I^2 = -1$.

15. An ellipsometer according to claim 13, wherein the values chosen are:

$t_k = T_k$, and $g_j$ such that D is the identity matrix.

16. An ellipsometer according to claim 9, wherein the means of detection and the processing unit are suitable for spectrographic measurements.

17. A process for calibration of the ellipsometer intended for measurement of a sample represented by the coefficients of a Mueller matrix (M), including:

a light source emitting an incident light beam, a polarizer, linearly polarising said incident beam, a polarization modulator modulating said incident beam, said sample receiving the modulated incident beam and returning a measurement beam, means to detect the measurement beam, producing electrical signals, and a processing unit receiving the electrical signals produced by the means of detection, wherein the polarization modulator is included in an optical component, the polarization modulator being a coupled modulator modulating the incident beam twice in succession, the two modulations being strictly at the same frequency of $\omega/2\pi$, and a coupling system coupling the modulations and modifying a polarization state of the light between the two modulations, so that the means of detection include a polarimeter producing n measured quantities ($I_1$–$I_n$) representing the polarization states of the measurement beam, and so that the processing unit produces, by Fourier transform, m values for each of the n measured quantities ($I_1$–$I_n$), with m being the number of components of each of the quantities measured, with n×m≦16 and m≧4 providing simultaneous access to the sixteen coefficients of the Mueller matrix (M); wherein since the polarizer and the polarization modulator constitute a polarization states generator, said polarization states generator and said means of detection respectively having a modulation matrix (W) and a detection matrix (A), the process comprising:

choosing a set of calibration identities which have known Mueller matrices (M), one of these entities being the identity matrix ($I_0$), for each of the calibration entities, adopting said entity as a sample in the ellipsometer, emitting an incident light beam which is polarized linearly with the light source and the polarizer, modulating the incident beam with the coupled modulator, sending the modulated incident beam to said entity, and returning a measurement beam, producing said measured quantities ($I_1$–$I_n$) by the means of detection and said values by the processing unit, and using said values, constructing a measured matrix (AMW), which is a product of the detection matrix (A), the Mueller matrix (M) of said entity and the modulation matrix, establishing a system of linear equations from the measured matrices (AMW), and solving this system in order to extract the modulation (W) and detection (A) matrices.

18. A calibration process in accordance with claim 17, wherein a set of entities is chosen including:

a linear polarizer at 0° on transmission, a linear polarizer at 45° on transmission, and a partial polarizer and phase shifter without singular values.

19. An ellipsometric measurement process intended for measurement of a sample represented by the coefficients of a Mueller matrix (M), in which:

emitting a linearly polarised incident light beam, modulating the incident beam with a polarization modulator, sending the modulated incident beam to the sample, and returning a measurement beam, detecting the measurement beam and produce electrical signals by the means of detection, and transmitting the electrical signals to a processing unit, characterized so that:

applying two successive phase modulations to the incident beam by means of a polarization modulator, the two modulations being strictly at the same frequency of $\omega/2\pi$, and being coupled by a system which modifies the polarization state of the light between the two modulations, producing n measured quantities ($I_1$–$I_n$) each representing a polarization state of the measurement beam using the means of detection, using a Fourier transform, producing m values for each of the n measured quantities by means of the processing unit, with $n \times m \geq 16$ and $m \geq 4$ allowing access to the sixteen coefficients of the Mueller matrix.

* * * * *